(12) United States Patent
Baughman et al.

(10) Patent No.: US 8,934,682 B2
(45) Date of Patent: *Jan. 13, 2015

(54) PROVIDING AN ID-VERIFIED BLOOD TEST

(75) Inventors: Aaron K. Baughman, Silver Spring, MD (US); Peter K. Malkin, Hawthorne, NY (US)

(73) Assignee: International Business Machines Corporation, Armonk, NY (US)

( * ) Notice: Subject to any disclaimer, the term of this patent is extended or adjusted under 35 U.S.C. 154(b) by 38 days.

This patent is subject to a terminal disclaimer.

(21) Appl. No.: 13/550,832

(22) Filed: Jul. 17, 2012

(65) Prior Publication Data

US 2014/0002235 A1 Jan. 2, 2014

Related U.S. Application Data

(63) Continuation of application No. 13/538,423, filed on Jun. 29, 2012.

(51) Int. Cl.
*G06K 9/00* (2006.01)
(52) U.S. Cl.
USPC ............... 382/124; 340/5.82; 340/426.11; 340/576; 382/218; 600/573
(58) Field of Classification Search
USPC .......... 382/124, 218; 600/110, 132, 310, 323, 600/583
See application file for complete search history.

(56) References Cited

U.S. PATENT DOCUMENTS

| | | | |
|---|---|---|---|
| 4,843,377 A | 6/1989 | Fuller et al. | |
| 5,876,326 A | 3/1999 | Takamura et al. | |
| 5,876,926 A | 3/1999 | Beecham | |
| 6,017,325 A | 1/2000 | Yerfino et al. | |
| 6,229,908 B1 * | 5/2001 | Edmonds et al. | 382/124 |
| 6,232,874 B1 * | 5/2001 | Murphy | 340/426.19 |
| 7,212,659 B2 | 5/2007 | Noro et al | |
| 7,415,138 B2 | 8/2008 | Schneider et al. | |
| 7,451,852 B2 | 11/2008 | Stewart et al. | |

(Continued)

FOREIGN PATENT DOCUMENTS

DE 202005020535 U1 9/2005

OTHER PUBLICATIONS

Sullivan, "Forensic Chemistry," Chemistry Encyclopedia, http://www.chemistryexplained.com/Fe-Ge/Forensic-Chemistry.html, Copyright 2012 Advameg, Inc.

(Continued)

*Primary Examiner* — Gregory M Desire
(74) *Attorney, Agent, or Firm* — Scully, Scott, Murphy & Presser, P.C.; Louis J. Percello, Esq.

(57) ABSTRACT

Providing an ID-verified blood test, in one aspect, may include enabling a user to press a finger against a fingerprint-reading panel and reading a fingerprint of the user. A blood sampling device coupled to the fingerprint-reading panel may be activated while the user has the finger against the fingerprint-reading panel to sample blood from the finger. Blood may be sampled from the user via the blood sampling device while the user has the finger against the fingerprint-reading panel. A test may be performed on the sampled blood to determine a level of specified chemical in the blood. User identification may be determined based on the fingerprint. The determined user identification and the level of the specified chemical may be returned.

19 Claims, 2 Drawing Sheets

(56) References Cited

U.S. PATENT DOCUMENTS

| | | |
|---|---|---|
| 7,637,634 B2 | 12/2009 | Chu |
| 8,581,711 B2 * | 11/2013 | Morgan et al. ............ 340/426.11 |
| 8,792,687 B2 * | 7/2014 | Baughman et al. ............ 382/124 |
| 2004/0085211 A1 | 5/2004 | Gotfried |
| 2005/0241871 A1 | 11/2005 | Stewart et al. |
| 2006/0253711 A1 | 11/2006 | Kallmann |
| 2006/0258918 A1 * | 11/2006 | Burd et al. .................... 600/310 |
| 2007/0239992 A1 | 10/2007 | White et al. |
| 2008/0139907 A1 * | 6/2008 | Rao et al. ...................... 600/323 |
| 2008/0289895 A1 | 11/2008 | Goi |
| 2009/0185726 A1 | 7/2009 | Higuchi |
| 2009/0227897 A1 | 9/2009 | Wendt et al. |
| 2009/0298049 A1 * | 12/2009 | Kurnool et al. .................. 435/5 |
| 2010/0010325 A1 | 1/2010 | Ridder et al. |
| 2011/0178382 A1 * | 7/2011 | Topp ............................. 600/365 |
| 2012/0268259 A1 | 10/2012 | Igel et al. |

OTHER PUBLICATIONS http://beaconbulletin.com/2011/05/16/uninvasive-dermal-alcohol-test/, May 16, 2011, retrieved Jun. 29, 2012.

International Search Report mailed Aug. 20, 2013 in corresponding International Application No. PCT/US13/36681.

U.S. Office Action mailed Sep. 27, 2013 in related U.S. Appl. No. 13/538,423.

Notice of Allowance mailed Mar. 17, 2014 in related U.S. Appl. No. 13/538,423.

* cited by examiner

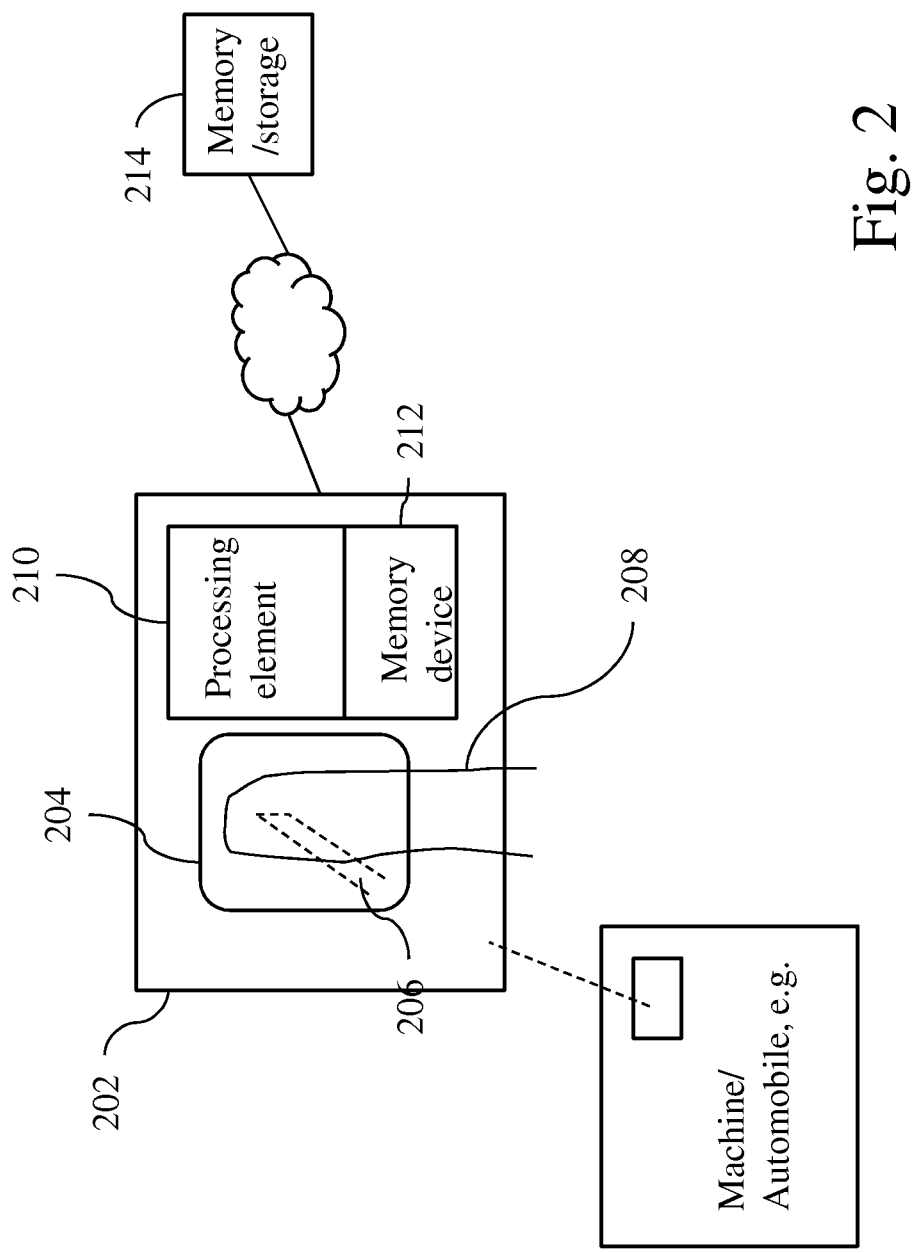

PROVIDING AN ID-VERIFIED BLOOD TEST

CROSS-REFERENCE TO RELATED APPLICATIONS

This application is a continuation of U.S. patent application Ser. No. 13/538,423 filed on Jun. 29, 2012, the entire contents of which are incorporated herein by reference.

FIELD

The present application relates generally to medical specimen testing and particularly to a device and a method thereof for verifying identification and simultaneously capturing specimen for testing.

BACKGROUND

Specimen samples such as blood samples of a subject, for instance, taken for medical tests, are usually manually associated with the subject. For example, samples of blood taken are manually labeled with the subject's identity. Such manual association does not provide a foolproof method for pairing a sample specimen with the subject's identify as there is always a chance of human error or even deceptive act of intentionally mislabeling the sample. With the existing methods, there is no way to ensure the identity of the person from whom a given sample of blood is drawn.

BRIEF SUMMARY

A method for providing an ID-verified blood test, in one aspect, may comprise enabling a user to press a finger against a fingerprint-reading panel. The method may also comprise reading a fingerprint of the user. The method may further comprise activating a blood sampling device coupled to the fingerprint-reading panel while the user has the finger against the fingerprint-reading panel to sample blood from the finger after the fingerprint is read. The method may also comprise sampling blood from the user via the blood sampling device while the user has the finger against the fingerprint-reading panel. The method may further comprise performing a test on the sampled blood to determine a level of specified chemical in the blood. The method may yet further comprise determining user identification based on the fingerprint. The method may also comprise returning the determined user identification and the level of the specified chemical.

A method for providing an ID-verified specimen sample test, in another aspect, may comprise enabling a user to press a part of the user's body portion from which to read an identification print against a scanner. The method may also comprise reading the identification print via the scanner. The method may further comprise actuating a specimen sampling device coupled to the scanner after the reading of the identification print while the user has the body portion pressed against the scanner; to sample specimen from the user's body portion. The method may also comprise sampling specimen via the sampling device. The method may further comprise performing a test on the sampled specimen to determine a level of specified chemical in the specimen. The method may yet further comprise determining whether the read identification print matches a pre-stored identification.

An apparatus for providing an ID-verified specimen sample test, in one aspect, may comprise a scanner operable to read an identification print from a body portion of a user in response to the user pressing the body portion on the scanner. The apparatus may also comprise a specimen sampling device coupled to the scanner, the specimen sampling device operable to sample specimen from the body portion while the user has the body portion pressed against the scanner. The apparatus may further comprise a processing element operable to determine user identification based on the scanned identification print and further operable to perform a test on the sampled specimen to determine a level of specified chemical in the specimen sample.

An apparatus for providing an ID-verified blood test, in one aspect, may comprise a fingerprint-reading panel operable to read a fingerprint of a user in response to the user pressing a finger on the fingerprint-reading panel. The apparatus may also comprise a blood sampling device coupled to the fingerprint-reading panel, the blood sampling device operable to sample blood from a user's finger while the user's finger is pressed against the fingerprint-reading panel. The apparatus may further comprise a processing element operable to determine user identification based on the fingerprint and further operable to perform a test on the sampled blood to determine a level of specified chemical in the blood.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

BRIEF DESCRIPTION OF THE SEVERAL VIEWS OF THE DRAWINGS

FIG. 2 is illustrates an apparatus for performing a medical test in one embodiment of the present disclosure.

DETAILED DESCRIPTION

Figure 1:
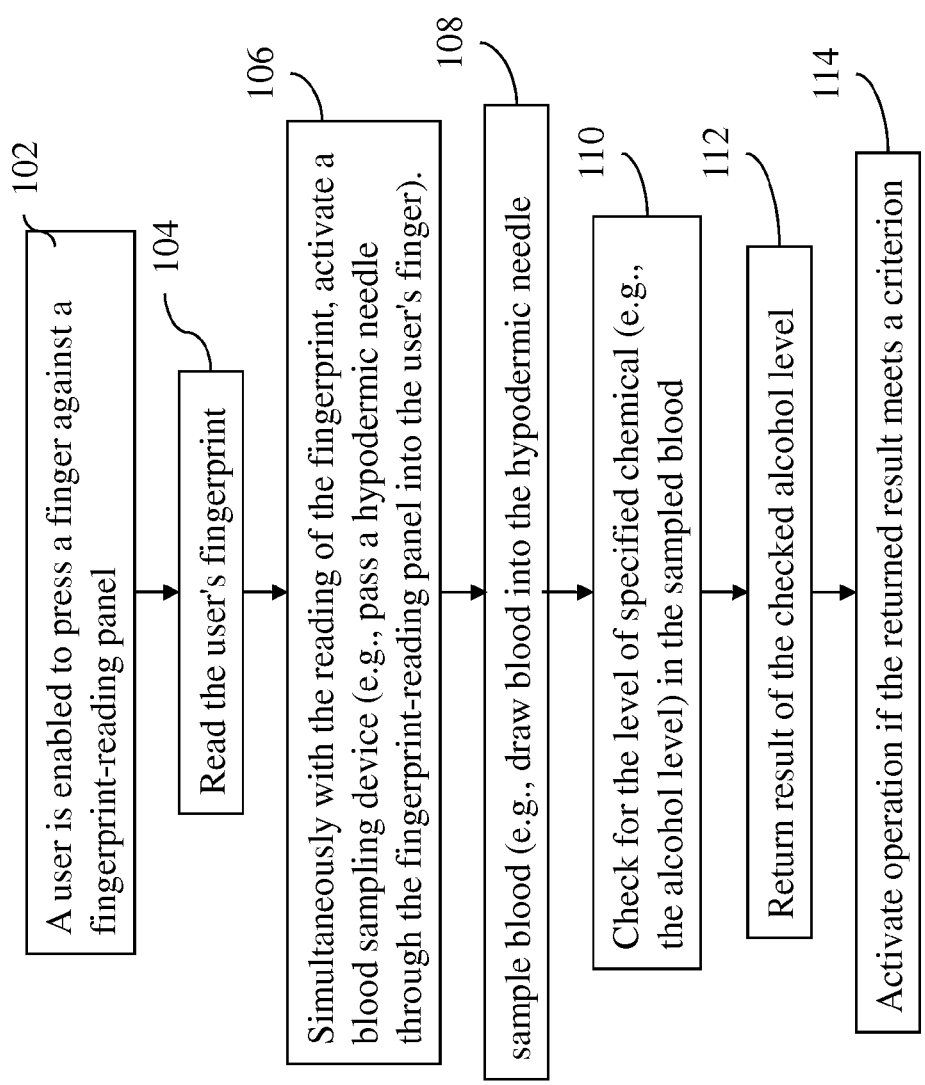
FIG. 1 is a flow diagram illustrating a method of providing an ID-verified blood test in one embodiment of the present disclosure.

A method and apparatus may be provided for identification (ID)-verified medical specimen. The method and apparatus may pair a physical personal identifier (like a finger print) with a physical personal indicator of personal physical condition (like a blood sample). For example, drawing blood through a panel verifies a given user's ID via their fingerprint while the user keeps their finger in contact with the given panel throughout the blood drawing process.

An apparatus of the present disclosure in one embodiment may comprise a needle and a fingerprint reader that is enabled to simultaneously take both the blood sample and fingerprint. The blood sample may be taken for various purposes, for example, to detect alcohol content, DNA identification, DNA correlation with a disease, glucose level, and others. Using a needle combined with fingerprint reader, the blood sample and fingerprint may be sampled simultaneously, and the fingerprint may be paired with a blood sample taken. In another embodiment of the present disclosure, a needle on the apparatus may be replaced with other means of sampling the blood or other bodily indicator—e.g., infrared detector (See. e.g., http colon slash slash (://) beaconbulletin dot (.) com/2011/05/16/uninvasive-dermal-alcohol-test/).

The method and apparatus (or device) of the present disclosure can be used in a testing apparatus that enables or prevents a person from starting and/or using a piece of equipment like: a vehicle or a large or otherwise dangerous piece of equipment—airplane, (nuclear) power plant equipment, saws, and others.

An example use scenario for the method and/or apparatus of the present disclosure may be a use in a secured car key. In this embodiment, a car ignition key may be provided that can only be used by a particular individual if their blood alcohol level is at a legal level. Assume that User1 is an individual with a DWI record that would otherwise keep them from maintaining their driving license. In place of User1's regular car key, User 1 may be a given a new key or like device augmented with the methodology of the present disclosure. The new key or the like device may include a fingerprint scanner and blood test retriever where the blood test retriever. The blood test retriever may a fine gauge hypodermic needle that protrudes up in the middle of the scanning pad. With the key, the user is required to complete the following:

User1 inserts the new key into the receptacle in the car's dashboard, and then presses their finger (e.g., thumb) onto the key's scanning pad.

In response to this pressure, the sample retrieving needle pricks User1's finger and draws a sample of blood.

Simultaneously, the scanner obtains User1's fingerprint from the finger touching the scanner surrounding the needle.

The key then verifies that the fingerprint matches User1 as well as ensuring the alcohol level in the blood sample is within legal limits.

If both the fingerprint matching and alcohol level tests pass, the key activates and User1 can turn it and start the car. Alternatively, if either test fails, then turning the key will not start car.

The methodology of the present disclosure in the above example scenario ensures that the user of the key is User1 and that it is User1's blood that is tested. Existing systems (e.g., breath testers and finger prick testers) do not provide such a preemptive car-start-blocking method which includes reliable ID determination.

As another example use for the methodology and/or the apparatus of the present disclosure may include a use as a secure healthcare ID and sample retrieval (e.g., HIV testing). In this example, the method provides retrieving fingerprint and blood sample pairs, where the fingerprint is guaranteed to be that of the person from whom the blood was drawn. Obtaining this assurance can be difficult in situations where test subjects are not comfortable with a given medical test. For example, with HIV testing, although subjects may be feel uncomfortable by the possible result of the testing, it is absolutely essential for the ID of a given test sample's source to be reliably known. By providing samples each with the fingerprint of the donor, the method of the present disclosure in one embodiment facilitates this requirement. In this example, the following process may be followed to obtain user's blood sample and fingerprint:

User2 presses their finger onto the retriever's scanning pad.

In response to this pressure, the retriever's sample retrieving needle ejects or extends up through the scanning pad into User2's finger and draws a sample of blood.

Simultaneously, the scanner obtains User2's fingerprint from the finger touching the scanner surrounding the needle.

The needed test results are obtained from the blood sample.

The results of the test are returned along with the scanned fingerprint. Note that if the User2's identify can be determined from the fingerprint, then this information (i.e., User2's ID) can be returned as well.

To ensure the returned data has not been falsified, the method of the present disclosure in one embodiment may provide a digital signature with each result. The signature may include a hash value which can be used to check that the result is not be modified.

Yet as another example use, the methodology and/or apparatus of the present disclosure in one embodiment may provide for a secure ID blood test retrieval method for random testing at work (e.g., healthcare or construction workers). In this scenario, the methodology and/or apparatus of the present disclosure may be used to provide highly reliable random blood testing. Here, the users being tested are workers at a particular construction site. With existing testing methods, violators may have escaped detection either by providing a test sample (e.g., of urine) that is not in fact theirs. Even with blood testing, a given individual may have a co-worker to stand to provide the blood. The methodology and/or apparatus of the present disclosure may preclude these means of avoiding detection. Testing method in this scenario may include:

User3 presses User3's finger onto the retriever's scanning pad.

In response to this pressure, the retriever's sample retrieving needle extends up through the scanning pad into User3's finger and draws a sample of blood.

Simultaneously, the scanner obtains User3's fingerprint from the finger touching the scanner surrounding the needle.

The needed test results are obtained from the blood sample.

The scanned fingerprint may be compared to those of the work site's employees to verify that the sample was in fact given by User3.

The blood sample is then tested to check User3's alcohol level.

The results of this blood test marked with User3's ID are then returned.

This process not only returns the result of the blood test, but a reliable indication of the blood donor's ID.

FIG. 1 is a flow diagram illustrating a method of providing an ID-verified blood test in one embodiment of the present disclosure. At 102, a user is enabled to press a finger against a fingerprint-reading panel. The fingerprint-reading panel may be a pressure sensitive fingerprint scanner. For example, a user may touch the panel with pressure on it. At 104, the user's fingerprint is read and recognized. At 106, a blood sample device coupled to the fingerprint-reading panel is activated, e.g., hypodermic needle is enabled to pass through the fingerprint-reading panel into the user's finger. In one aspect, in order to guarantee that the blood sample is drawn from the correct users' finger, the needle does not pass through the fingerprint reading panel into the user's finger anytime before the user's finger print is scanned. At 108, blood is sampled, e.g., blood is drawn into the hypodermic needle. The user continues to keep the finger pressed against the fingerprint-reading panel until the extraction is complete. In one aspect, directly drawing the subject's blood allows for correct results even for those subjects whose finger pads may have become highly calloused. At 110, the drawn blood is checked for alcohol level. At 112, the result of the test is returned.

At 114, based on the purpose for the method and the result, various automatic procedures may follow. For instance, if the method is used in a device for activating a start of a machine (e.g., automobile, heavy machinery, chainsaw, gun trigger lock or others), the activation of such a machine occurs if and only if the alcohol level of the extracted blood is in an acceptable range.

With the methodology of the present disclosure, other checks may be performed, for example, for abnormal/existence of particular drug (e.g., level of prescribed drug below safe level, or presence of a recreational drug, sugar or insulin level.

In another aspect, the method may be set to recognize only a single pre-specified user. In another aspect, the finger-print reading panel verifies that it is human skin and not a false fingerprint reproduction pressed against it.

In another embodiment, the user's blood is tested non-invasively through the fingerprint-reading panel, for instance, with an infrared detector.

The methodology of the present disclosure in one embodiment ensures that the biometric identify identification and blood sample are drawn from the same individual.

FIG. 2 illustrates an apparatus for performing a medical test in one embodiment of the present disclosure. The apparatus 202 may include a scanner 204 enabled to retrieve a given test subject's fingerprint. A test sample retrieval device, e.g., a finger-prick needle 206, may be located on the scanner 204. The needle 206 is enabled to actuate, come out, from the scanner into the scanned finger 208, e.g., the middle of the scanned finger. The device 202 also includes a processing element 210, coupled to the scanner which uses the scanner to obtain the test subject's fingerprint and sample or draw blood from this finger using the test sample retriever. The processor element 210 first determines the test subject's ID by comparing the scanned fingerprint to one or more fingerprint data it has stored in local memory 212. If the scanned fingerprint matches one of those known to it (e.g., stored in local memory 212), the processing element 210 performs a test on the retrieved sample, and returns the test result when finished. The fingerprints known to the processing device 210 may have the ID's associated with each fingerprint, the ID being that of each fingerprint's owner. The device may also return the ID associated with the matched fingerprint. In addition, rather than being held in the devices local memory, the fingerprints and associated ID's may be stored on a remote data source 214 and accessed by the processing element 210 via network communication, e.g., wifi, Bluetooth, or via the Internet or another global or local wireless and/or wired networking. It should be understood that the device 210 need not be limited to the elements or components shown in FIG. 2. For example, the device 210 may further include other components such as universal serial bus (USB) interface for connecting to another device, other communication interfaces, device interfaces and/or other components.

The returned result may be a value that is set to True or False, or a binary value 1 or 0, or another representation of such status. The returned result is true if and only if the scanned fingerprint matches that of one of the fingerprints known to the processing element 210 and if the test (e.g., an alcohol level) of the retrieved sample succeeds, e.g., meets a threshold criterion.

The returned result may include both indication of subject's ID as determined by the fingerprint comparison, and the test results, e.g., indication of the subject's blood alcohol level. In another aspect, the returned result may also include a digital signature (e.g., MD5) that ensures the indicated data has not been modified.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages, a scripting language such as Perl, VBS or similar languages, and/or functional languages such as Lisp and ML and logic-oriented languages such as Prolog. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The computer program product may comprise all the respective features enabling the implementation of the methodology described herein, and which—when loaded in a computer system—is able to carry out the methods. Computer program, software program, program, or software, in the present context means any expression, in any language, code or notation, of a set of instructions intended to cause a system having an information processing capability to perform a particular function either directly or after either or both of the following: (a) conversion to another language, code or notation; and/or (b) reproduction in a different material form.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Various aspects of the present disclosure may be embodied as a program, software, or computer instructions embodied in a computer or machine usable or readable medium, which causes the computer or machine to perform the steps of the method when executed on the computer, processor, and/or machine. A program storage device readable by a machine, tangibly embodying a program of instructions executable by the machine to perform various functionalities and methods described in the present disclosure is also provided.

The system and method of the present disclosure may be implemented and run on a general-purpose computer or special-purpose computer system. The terms "computer system" and "computer network" as may be used in the present application may include a variety of combinations of fixed and/or portable computer hardware, software, peripherals, and storage devices. The computer system may include a plurality of individual components that are networked or otherwise linked to perform collaboratively, or may include one or more stand-alone components. The hardware and software components of the computer system of the present application may include and may be included within fixed and portable devices such as desktop, laptop, and/or server. A module may be a component of a device, software, program, or system that implements some "functionality", which can be embodied as software, hardware, firmware, electronic circuitry, or etc.

The embodiments described above are illustrative examples and it should not be construed that the present invention is limited to these particular embodiments. Thus, various changes and modifications may be effected by one skilled in the art without departing from the spirit or scope of the invention as defined in the appended claims.

We claim:

1. An apparatus for providing an ID-verified blood test, comprising:
   a fingerprint-reading panel operable to read a fingerprint of a user in response to the user pressing a finger on the fingerprint-reading panel;
   a blood sampling device coupled to the fingerprint-reading panel, the blood sampling device operable to sample blood from a user's finger while the user's finger is pressed against the fingerprint-reading panel; and
   a processing element operable to determine user identification based on the fingerprint and further operable to perform a test on the sampled blood to determine a level of specified chemical in the blood,
   wherein the apparatus is included in a key given to the user for activating a machine,
   wherein the key is operable to read and sample, in response to the user inserting the key into a receptacle of the machine,
   wherein the key activates the machine only if the determined user identification matches a pre-stored identification associated with the key given to the user and the determined level of alcohol meets a threshold criterion.

2. The apparatus of claim 1, wherein the machine includes an automobile, a heavy machinery equipment, or a transportation vehicle, or combinations thereof.

3. The apparatus of claim 1, wherein the specified chemical includes alcohol.

4. The apparatus of claim 1, wherein the specified chemical includes sugar.

5. The apparatus of claim 1, wherein the specified chemical includes a drug.

6. The apparatus of claim 1, wherein the blood sampling device includes a hypodermic needle.

7. The apparatus of claim 1, wherein the blood sampling device includes an infrared detector.

8. The apparatus of claim 1, wherein the user is required to continue to keep the finger pressed against the fingerprint reading panel until the sampling of the blood is completed.

9. The apparatus of claim 1, wherein the key is associated with a single user.

10. A computer readable storage medium storing a program of instructions executable by a machine to perform a method of providing an ID-verified blood test, comprising:
    enabling a user to press a finger against a fingerprint-reading panel incorporated in a key provided for use only by a particular individual, the key for activating a machine;
    reading a fingerprint of the user;
    activating a blood sampling device coupled to the fingerprint-reading panel while the user has the finger against the fingerprint-reading panel to sample blood from the finger after the fingerprint is read;
    sampling blood from the user via the blood sampling device while the user has the finger against the fingerprint-reading panel;
    performing a test on the sampled blood to determine a level of specified chemical in the blood;
    determining user identification based on the fingerprint; and
    activating the key to actuate the machine only if the determined user identification matches the particular individual associated with the key and the determined level of specified chemical meets a threshold criterion,
    wherein the reading, the activating of the blood sample device, the sampling, the performing and the determining are performed in response to the user inserting the key into a receptacle of the machine.

11. The computer readable storage medium of claim 10, wherein the machine includes an automobile, a heavy machinery equipment, or a transportation vehicle, or combinations thereof.

12. The computer readable storage medium of claim 10, wherein the specified chemical includes alcohol.

13. The computer readable storage medium of claim 10, wherein the specified chemical includes sugar.

14. The computer readable storage medium of claim 10, wherein the specified chemical includes a drug.

15. The computer readable storage medium of claim 10, wherein the blood sampling device includes a hypodermic needle.

16. The computer readable storage medium of claim 10, wherein the blood sampling device includes an infrared detector.

17. The computer readable storage medium of claim 10, wherein the user is required to continue to keep the finger pressed against the fingerprint reading panel until the sampling of the blood is completed.

18. The computer readable storage medium of claim 10, wherein the key is associated with a single user.

19. An apparatus for providing an ID-verified specimen sample test, comprising:
    a scanner operable to read an identification print from a body portion of a user in response to the user pressing the body portion on the scanner;
    a specimen sampling device coupled to the scanner, the specimen sampling device operable to sample specimen from the body portion while the user has the body portion pressed against the scanner; and
    a processing element operable to determine user identification based on the scanned identification print and further operable to perform a test on the sampled specimen to determine a level of specified chemical in the specimen sample,
    wherein the apparatus is included in a key given to the user for activating a machine,
    wherein the key is operable to read and sample, in response to the user inserting the key into a receptacle of the machine
    wherein the key activates the machine only if the determined user identification matches a pre-stored identification associated with the key given to the user and the determined level of alcohol meets a threshold criterion.

* * * * *